(12) United States Patent
Goble et al.

(10) Patent No.: US 6,565,560 B1
(45) Date of Patent: May 20, 2003

(54) ELECTROSURGICAL INSTRUMENT

(75) Inventors: Nigel M Goble, Nr Cardiff (GB); Colin CO Goble, South Glamorgan (GB); Alan N Syrop, Cardiff (GB)

(73) Assignee: Gyrus Medical Limited, Cardiff (GB)

( * ) Notice: Subject to any disclaimer, the term of this patent is extended or adjusted under 35 U.S.C. 154(b) by 0 days.

(21) Appl. No.: 09/462,927

(22) PCT Filed: Jul. 15, 1998

(86) PCT No.: PCT/GB98/02094

§ 371 (c)(1),
(2), (4) Date: Mar. 27, 2000

(87) PCT Pub. No.: WO99/03409

PCT Pub. Date: Jan. 28, 1999

(30) Foreign Application Priority Data

Jul. 18, 1997 (GB) .............................. 9715200

(51) Int. Cl.[7] .............................. A61B 18/18
(52) U.S. Cl. .............. 606/41; 606/45; 606/48; 606/167; 606/171; 606/180
(58) Field of Search ........... 606/41, 42, 45–50, 606/167, 171, 180; 604/22

(56) References Cited

U.S. PATENT DOCUMENTS

| | | | |
|---|---|---|---|
| 4,706,667 A | 11/1987 | Roos | |
| 5,411,514 A | * | 5/1995 | Fucci et al. ............... 606/180 |
| 5,451,223 A | 9/1995 | Ben-Simhon | |
| 5,527,331 A | 6/1996 | Kresch et al. | |
| 5,735,846 A | 4/1998 | Panescu et al. | |
| 5,776,092 A | 7/1998 | Farin et al. | |
| 5,810,809 A | 9/1998 | Rydell | |
| 5,814,044 A | * | 9/1998 | Hooven ..................... 604/21 |
| 5,904,681 A | 5/1999 | West, Jr. | |
| 5,941,876 A | 8/1999 | Nardella et al. | |

FOREIGN PATENT DOCUMENTS

| | | |
|---|---|---|
| EP | 0 754 437 | 1/1997 |
| EP | 754437 | 1/1997 |
| WO | WO 97/00646 | 1/1997 |
| WO | WO 97/00647 | 1/1997 |
| WO | 9717027 | 5/1997 |
| WO | WO 97/24993 | 7/1997 |

* cited by examiner

Primary Examiner—Rosiland S. Kearney
(74) Attorney, Agent, or Firm—Nixon & Vanderhye P.C.

(57) ABSTRACT

An electrosurgical instrument is provided for the treatment of tissue in the presence of an electrically-conductive fluid medium. The instrument comprises an instrument shaft (10), a tissue treatment electrode (12) at one end of the shaft, and removal means, the instrument having an apertured portion (20a) through which matter can be aspirated by the removal means from the region surrounding the tissue treatment electrode. The removal means comprises a channel formed within the instrument shaft (10) and leading from the apertured portion (20a). The channel is provided with agitation means (14) for preventing the build-up of sublimation products within the channel.

31 Claims, 5 Drawing Sheets

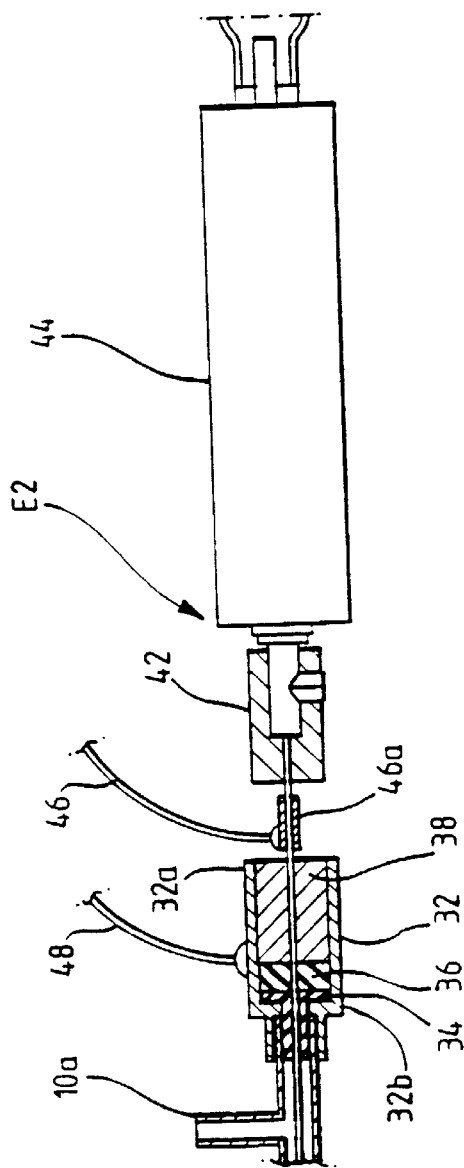
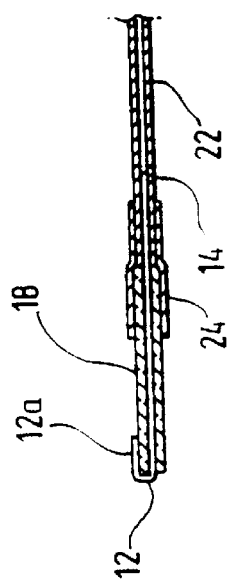
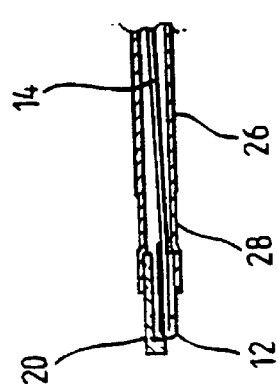
Fig. 4.
Fig. 5.

ELECTROSURGICAL INSTRUMENT

This application is the U.S. national phase of International Application No. PCT/GB98/02094, filed Jul. 15, 1998.

This invention relates to an electrosurgical instrument for the treatment of tissue in the presence of an electrically-conductive fluid medium, to electrosurgical apparatus including such an instrument, and to an electrode unit for use in such an instrument. Endoscopic electrosurgery is useful for treating tissue in cavities of the body, and is normally performed in the presence of a distension medium. When the distension medium is a liquid, this is commonly referred to as underwater electrosurgery, this term denoting electrosurgery in which living tissue is treated using an electrosurgical instrument with a treatment electrode or electrodes immersed in liquid at the operation site. A gaseous medium is commonly employed when endoscopic surgery is performed in a distensible body cavity of larger potential volume in which a liquid medium would be unsuitable, as is often the case in laparoscopic or gastroenterological surgery.

Underwater surgery is commonly performed using endoscopic techniques, in which the endoscope itself may provide a conduit (commonly referred to as a working channel) for the passage of an electrode. Alternatively, the endoscope may be specifically adapted (as in a resectoscope) to include means for mounting an electrode, or the electrode may be introduced into a body cavity via a separate access means at an angle with respect to the endoscope—a technique commonly referred to as triangulation. These variations in technique can be subdivided by surgical speciality, where one or other of the techniques has particular advantages given the access route to the specific body cavity. Endoscopes with integral working channels, or those characterised as resectoscopes, are generally employed when the body cavity may be accessed through a natural body opening—such as the cervical canal to access the endometrial cavity of the uterus, or the urethra to access the prostate gland and the bladder. Endoscopes specifically designed for use in the endometrial cavity are referred to as hysteroscopes, and those designed for use in the urinary tract include cystoscopes, urethroscopes and resectoscopes. The procedures of transurethal resection or vaporisation of the prostate gland are known as TURP and EVAP respectively. When there is no natural body opening through which an endoscope may be passed, the technique of triangulation is commonly employed. Triangulation is commonly used during underwater endoscopic surgery on joint cavities such as the knee and the shoulder. The endoscope used in these procedures is commonly referred to as an arthroscope.

Electrosurgery is usually carried out using either a monopolar instrument or a bipolar instrument. With monopolar electrosurgery, an active electrode is used in the operating region, and a conductive return plate is secured to the patient's skin. With this arrangement, current passes from the active electrode through the patient's tissues to the external return plate. Since the patient represents a significant portion of the circuit, input power levels have to be high (typically 150 to 250 watts), to compensate for the resistive current limiting of the patient's tissues and, in the case of underwater electrosurgery, power losses due to the fluid medium which is rendered partially conductive by the presence of blood or other body fluids. Using high power with a monopolar arrangement is also hazardous, due to the tissue heating that occurs at the return plate, which can cause severe skin burns. There is also the risk of capacitive coupling between the instrument and patient tissues at the entry point into the body cavity.

With bipolar electrosurgery, a pair of electrodes (an active electrode and a return electrode) are used together at the tissue application site. This arrangement has advantages from the safety standpoint, due to the relative proximity of the two electrodes so that radio frequency currents are limited to the region between the electrodes. However, the depth of effect is directly related to the distance between the two electrodes; and, in applications requiring very small electrodes, the inter-electrode spacing becomes very small, thereby limiting tissue effect and the output power. Spacing the electrodes further apart would often obscure vision of the application site, and would require a modification in surgical technique to ensure direct contact of both electrodes with the tissue.

There are a number of variations to the basic design of the bipolar probe. For example, U.S. Pat. No. 4,706,667 describes one of the fundamentals of the design, namely that the ratio of the contact areas of the return electrode and of the active electrode is greater than 7:1 and smaller than 20:1 for cutting purposes. This range relates only to cutting electrode configurations. When a bipolar instrument is used for desiccation or coagulation, the ratio of the contact areas of the two electrodes may be reduced to approximately 1:1 to avoid differential electrical stresses occurring at the contact between the tissue and the electrode.

The electrical junction between the return electrode and tissue can be supported by wetting of the tissue by a conductive solution such as normal saline. This ensures that the surgical effect is limited to the active electrode, with the electric circuit between the two electrodes being completed by the tissue. One of the obvious limitations with the design is that the active electrode (typically a needle) must be completely buried in the tissue to enable the return electrode to complete the circuit. Another problem is one of the orientation: even a relatively small change in application angle from the ideal perpendicular contact with respect to the tissue surface, will change the contact area ratio, so that a surgical effect can occur in the tissue in contact with the return electrode.

Cavity distension provides space for gaining access to the operation site, to improve visualisation, and to allow for manipulation of instruments. In low volume body cavities, particularly where it is desirable to distend the cavity under higher pressure, liquid rather than gas is more commonly used due to better optical characteristics, and because it washes blood away from the operative site.

Conventional underwater electrosurgery has been performed using a non-conductive liquid (such as 1.5% glycine) as an irrigant, or as a distension medium to eliminate electrical conduction losses. Glycine is used in isotonic concentrations to prevent osmotic changes in the blood when intra-vascular absorption occurs. In the course of an operation, veins may be severed, with resultant infusion of the liquid into the circulation, which could cause, among other things, a dilution of serum sodium which can lead to a condition known as water intoxication.

The applicants have found that it is possible to use a conductive liquid medium, such as normal saline, in underwater endoscopic electrosurgery in place of non-conductive, electrolyte-free solutions. Normal saline is the preferred distension medium in underwater endoscopic surgery when electrosurgery is not contemplated, or a non-electrical tissue effect such as laser treatment is being used. Although normal saline (0.9% w/v; 150 mmol/l) has an electrical conductivity somewhat greater than that of most body tissue, it has the advantage that displacement by absorption or extravasation from the operative site produces little physiological effect, and the so-called water intoxication effects of non-conductive, electrolyte-free solutions are avoided.

Carbon dioxide is the preferred gaseous distension medium, primarily because of its non-toxic nature and high water solubility.

The applicants have developed a bipolar instrument suitable for underwater electrosurgery using a conductive liquid or gaseous medium. This electrosurgical instrument for the treatment of tissue in the presence of a fluid medium, comprises an instrument body having a handpiece and an instrument shaft and an electrode assembly, at one end of the shaft. The electrode assembly comprises a tissue treatment (active) electrode which is exposed at the extreme distal end of the instrument, and a return electrode which is electrically insulated from the tissue treatment electrode and has a fluid contact surface spaced proximally from the exposed part of the tissue treatment electrode. In use of the instrument, the tissue treatment electrode is applied to the tissue to be treated whilst the return electrode, being spaced proximally from the exposed part of the tissue treatment electrode, is normally spaced from the tissue and serves to complete an electrosurgical current loop from the tissue treatment electrode through the tissue and the fluid medium. This electrosurgical instrument is described in the specification of our International Patent Application No. PCT/GB96101473.

The electrode structure of this instrument, in combination with an electrically-conductive fluid medium largely avoids the problems experienced with monopolar or bipolar electrosurgery. In particular, input power levels are much lower than those generally necessary with a monopolar arrangement (typically 100 watts). Moreover, because of the relatively large spacing between its electrodes, an improved depth of effect is obtained compared with conventional bipolar arrangements.

The specification of our International Patent Application No. GB96/01472 describes an irrigated bipolar electrosurgical instrument that can be used in open air or gas-filled environments. This instrument includes an internal channel for feeding electrically-conductive fluid (typically saline) to the exposed end of a tissue treatment electrode so as to provide a conductive fluid path that completes an electrical circuit to a return electrode when the instrument is in use. This instrument also includes an internal channel for removing fluid from the region of the exposed end of the tissue treatment electrode. When the fluid is a liquid, such as saline, the presence of that liquid can cause collateral tissue damage, so its removal is desirable. This type of instrument is intended primarily for use in open air or gas-filled environments, and is not suitable for use with electrosurgical procedures which require distension of a body cavity.

However, where the volume of a body cavity is small—for example in arthroscopic surgery where even the large joints, such as the knee, may only accommodate 50–60 ml of irrigation fluid—the following problems may occur, namely:

(i) Heated fluid in the immediate vicinity of the tissue contact electrode can cause collateral tissue damage;

(ii) The products of the tissue vaporised by the tissue contact electrode can cause visualisation problems; and (iii) Soft tissue present in a joint space tends to move about, making it difficult to apply the active electrode to vaporise such tissue.

An arthroscope electrode may be characterised as short (100 to 140 mm), and rigid with a working diameter up to 5 mm. It can be introduced through a stab incision into a joint cavity (with or without a cannula) using the triangulation technique. Such an electrode is operated with a motion which moves the electrode between the 9 O'Clock and 3 O'Clock positions on the arthroscopic image. As a result, the tissue to be treated is usually approached at a shallow working angle with respect to the axis of the electrode. An arthroscopic electrode thus needs to have an effect consistent with this angled approach to the tissue. The tissue to be treated, such as meniscal cartilage, is commonly dense and of a high electrical impedance. An arthroscope electrode requires output power and voltage settings that reflect the type of tissue being treated, the size of electrode, and the fact that arthroscopists are seeking a speed of effect comparable to that of the mechanical shaver devices they currently employ, albeit with an electrode of smaller dimensions than a shaver blade for improved access.

The specification of our British Patent Application 9612993.7 describes an electrosurgical instrument for the treatment of tissue in the presence of an electrically-conductive fluid medium. The instrument comprises an instrument shaft, and an electrode assembly at one end of the shaft, the electrode assembly comprising a tissue treatment electrode and a return electrode which is electrically insulated from the tissue treatment electrode by means of an insulation member. The tissue treatment electrode has an exposed end for treating tissue, and the return electrode has a fluid contact surface which is spaced from the tissue treatment electrode in such a manner as to define, in use, a conductive fluid path that completes an electrical circuit between the tissue treatment electrode and the return electrode. The electrode assembly is provided with a plurality of apertures in the region of the tissue treatment electrode, through which apertures vapour bubbles and/or particulate material can be aspirated from the region surrounding the tissue treatment electrode.

An RF generator is provided for powering the electrode assembly. The power required from the RF generator to achieve vaporisation depends on a number of variables more fully described in the specification of our International Patent Application No. GB97/00065. Of these variables two, are of particular importance in the context of the present invention; one being the cooling effect produced by the aspiration of conductive fluid in the region of the tissue contact electrode, and the other being the disruption of the vapour pocket formed around the tissue contact electrode by the flow of conductive fluid. These problems can be partially overcome by coordinating the aspiration by monitoring the output features of the generator which indicate the vaporisation power threshold has been exceeded. This usually results in a series of suction pulses as the vaporisation threshold is repeatedly exceeded between pulses and then elevated during the suction pulses so that, should vaporisation be maintained, the suction will be applied continuously. By using this technique, heated saline in the vicinity of the tissue contact electrode and vaporisation products can be successfully removed. The other desirable feature is the aspiration of loose tissue towards the tissue contact electrode, so that it can be stabilised during vaporisation. Whilst this can be achieved according to this technique; there are two significant performance limitations.

The first of these limitations is that the gaseous products of tissue vaporisation contain fatty products which have a sublimation property, i.e. they condense directly to a solid; sublimation occurring at temperatures well above boiling point. As the electrode shaft within the body cavity is cooled by the surrounding saline, these products are easily condensed. Thus, if a parallel suction shaft is used, the build up is along its entire length, and eventually completely blocks the tube. This process, even at the flow rates dictated by minimal influence on the power threshold, can cause very rapid blocking. For example, it is found that, with a moderately large electrode tip, using a 1 mm internal diameter suction tube, complete blockage occurs after 30 seconds of activation. Obviously, a larger tube bore would increase the time before blockage, but this occurs so rapidly that the required bore size for a useful electrode life is beyond the dimensions of the maximum shaft diameter. The problems of sublimation are compounded by aspiration of tissue pieces which are incompletely vaporised before being excised from the remainder of the tissue. Given the need to attract tissue and, therefore, the requirement for a strong suction pressure which, once tissue is engaged with the tissue contact electrode and the vaporisation threshold is continually exceeded by cessation of flow, increases the propensity for aspiration of unvaporised tissue and blockage of the aspiration channel.

The second of these limitations also relates to adherence of tissue to the tissue contact electrode. As indicated above, once the tissue obstructs flow, the vaporisation power threshold is exceeded, and suction is continuously applied. Under these circumstances, and particularly when aspiration channels are provided adjacent to the tissue treatment electrode, a steady state can be reached wherein the tissue is held around the periphery of the tissue contact electrode, the portion of tissue in the immediate vicinity of the tissue treatment electrode is vaporised but, without moving the application site or redirecting suction solely through the tissue treatment electrode, no further removal of tissue will occur. For example, large pieces of tissue tend to bridge the tissue treatment electrode, so that all tissue in contact with the electrode is removed, but the bulk of the tissue is left in place. Applying suction solely through the tissue treatment electrode limits the size of the electrode otherwise two extremes are created where, on the one hand during activation in conductive fluid, the vaporisation power threshold is very elevated despite synchronising suction pulses with the RF output, typically >200 Watts, yet, on the other hand, can be reduced to below 50% of this level once tissue is engaged. With a static tissue contact electrode, there is an inevitable compromise between these performances variables.

The aim of the invention to provide an improved electrosurgical instrument of this type.

The present invention provides an electrosurgical instrument for the treatment of tissue in the presence of an electrically-conductive fluid medium, the instrument comprising an instrument shaft, a tissue treatment electrode mounted at the distal end of the shaft, and removal means, the instrument having an apertured portion through which matter can be aspirated by the removal means from the region surrounding the tissue treatment electrode, the removal means comprising a channel formed within the instrument shaft and leading from the apertured portion, wherein the channel is provided with agitation means movable relative thereto.

The agitation means thus prevents the build-up of sublimation products within the channel.

The instrument may further comprise drive means for moving the tissue treatment electrode relative to the distal end of the shaft.

Advantageously, the instrument further comprises a return electrode which is electrically insulated from the tissue treatment electrode by insulation means, the tissue treatment electrode being exposed at the distal end of the instrument, and the return electrode having a fluid contact surface spaced proximally from the exposed end of the tissue treatment electrodes.

In a preferred embodiment, the tissue treatment electrode is movable cyclically relative to the return electrode so as to move the tissue treatment electrode into, and out of, at least one position in which arcing occurs between the tissue treatment and return electrode.

Preferably, the channel is defined by the instrument shaft, and the agitation means is constituted by a rod mounted within, and movable relative to, the instrument shaft.

Conveniently, the tissue treatment electrode is constituted by the distal end portion of the rod. Thus, movement of the rod results in movement of the tissue treatment electrode, and this prevents tissue bridging, as the tendency for tissue to obstruct the channel is obviated by the electrode movement ensuring that such tissue is treated. Tissue can, therefore, be electrosurgically removed from an operation site by a vaporisation technique, and can be electrosurgically morcellated (that is to say chewed up) in this region by the moving tissue treatment electrode, this process being analogous to a miniature liquidiser.

Advantageously, the rod is constituted by a tungsten wire having a diameter in the range of from 0.2 mm to 1.0 mm. Preferably, the tungsten wire has a diameter in the range of from 0.4 mm to 0.6 mm.

Advantageously, the tissue treatment electrode is angled with respect to the longitudinal axis of the instrument shaft, and the instrument further comprises an insulating sleeve surrounding the rod proximally of said angled end portion. The insulating sleeve may be a ceramic sleeve.

Preferably, the instrument further comprises an insulation member provided at the distal end of the instrument shaft, the insulation member defining said apertured region. The insulation member may be made of a ceramic material.

Advantageously, the insulation member is formed with a slot which constitutes the apertured region, the tissue treatment electrode passing through the slot. Alternatively, the apertured region is constituted by a gap between the tissue treatment electrode and the insulation member.

In a preferred embodiment, the drive means is such as to reciprocate the rod within the channel. Advantageously, the drive means is constituted by a motor and coupling means for convening the rotary output of the motor into reciprocatory movement of the rod.

In this case, the angled end portion of the rod may be at right-angles to the longitudinal axis of the instrument shaft, and the tip of the angled end portion may constitute the tissue contacting portion of the tissue treatment electrode. This electrode is, therefore, a side effect electrode.

In another preferred embodiment, the drive means is such as to rotate the rod within the channel. An electric motor may constitute the drive means.

In this case, the drive rod may be formed with a portion off-set from the longitudinal axis of the instrument shaft.

Advantageously, the angled end portion of the rod is at right-angles to the longitudinal axis of the instrument shaft, and the distal end surface of said angled end portion constitutes the tissue contacting portion of the tissue treatment electrode. The rotation of the angled end portion of the rod permits the use of a small diameter rod, and hence the use of a small tissue treatment electrode, whilst providing a relatively large area tissue contacting position. The use of a small diameter tissue treatment electrode also permits the use of lower electrosurgical powers and/or higher fluid medium flow rates.

Alternatively, the angled end portion of the rod makes an acute angle with the longitudinal axis of the instrument shaft, and the insulation member is provided with an inclined cam surface which is engagable with the apex of the angled end portion of the rod.

It is also possible for the angled end portion of the rod to be bent back around the distal end portion of the insulating sleeve.

Preferably, the removal means further comprises a pump connected to the channel at a region thereof remote from the apertured portion of the instrument. The pump may be activated cyclically whereby matter is aspirated by the removal means in a pulsed fashion. Conveniently, the pump is activated only when the tissue treatment electrode is powered for tissue vaporisation.

The instrument may further comprise an RF generator having a bipolar output connected to the tissue treatment electrode and the return electrode. Advantageously, the RF generator supplies energy to the drive means. Preferably, the pump is controlled in dependence upon the output characteristics of the RF generator.

The electrosurgical instrument of the invention is useful for dissection, resection, vaporisation, desiccation and coagulation of tissue, as well as for combinations of these functions. It has a particular application in arthroscopic surgery as it pertains to endoscopic and percutaneous procedures performed on joints of the body including, but not limited to, such techniques as they apply to the spine and other non-synovial joints. Arthroscopic operative procedures may include: partial or complete meniscectomy of the knee joint including meniscal cystectomy; lateral retinacular release of the knee joint; removal of anterior and posterior cruciate ligaments or remnants thereof; labral tear resection, acromioplasty, bursectomy and subacromial decompression of the shoulder joint; anterior release of the temperomandibular joint; synovectomy, cartilage debridement, chondroplasty, division of intra-articular adhesions, fracture and tendon debridement as applied to any of the synovial joints of the body; inducing thermal shrinkage of joint capsules as a treatment for recurrent dislocation, subluxation or repetitive stress injury to any articulated joint of the body; discectomy either in the treatment of a disc prolapse or as part of a spinal fusion via a posterior or anterior approach to the cervical, thoracic and lumbar spine or any other fibrous joint for similar purposes; excision of diseased tissue; and haemostasis.

The instrument of the invention is also useful for dissection, resection, vaporisation, desiccation and coagulation of tissue, as well as combinations of these functions, with particular application in urological endoscopic (urethroscopy, cystoscopy, ureteroscopy and nephroscopy) and percutaneous surgery. Urological procedures may include: electro-vaporisation of the prostate gland (EVAP) and other variants of the procedure commonly referred to as transurethral resection of the prostate (TURP) including, but not limited to, interstitial ablation of the prostate gland by a percutaneous or perurethral route whether performed for benign or malignant disease; transurethral or percutaneous resection of urinary tract tumours as they may arise as primary or secondary neoplasms, and further as they may arise anywhere in the urological tract from the calyces of the kidney to the external urethral meatus; division of strictures as they may arise at the pelviureteric junction (PUJ), ureter, ureteral orifice, bladder neck or urethra; correction of ureterocoele; shrinkage of bladder diverticular; cystoplasty procedures as they pertain to corrections of voiding dysfunction; thermally induced shrinkage of the pelvic floor as a corrective treatment for bladder neck descent; excision of diseased tissue; and haemostasis.

The electrosurgical instrument of the invention is also useful for dissection, resection, vaporisation, desiccation and coagulation of tissue and combinations of these functions with particular application in laparascopic, colposcopic (including vaginal speculum) and open surgical procedures on the female genital tract and adnexal related diseases. Laparascopic operative procedures may include: removal of subserosal and pedunculated fibroids, ablation of ectopic endometrium, ovarian cystectomy and ovarian drilling procedures; oophorectomy, salpingo-oophorectomy, subtotal hysterectomy and laparaoscopically assisted vaginal hysterectomy (LAVH) as may be performed for benign or malignant diseases; laparoscopic uterosacral nerve ablation (LUNA); fallopian tube surgery as correction of ectopic pregnancy or complications arising from acquired obstructions; division of abdominal adhesions; and haemostasis.

The electrosurgical instrument of the invention is also useful in the lower female genital tract, including treatment of cervix, vagina and external genitalia whether accessed directly or using instrumentation comprising generally speculae and colposcopes. Such applications include: vaginal hysterectomy and other pelvic procedures utilising vaginal access; LLETZ/LEEP procedure (large loop excision of the transformation zone) or excision of the transformation zone of the endocervix; removal of cystic or septic lesions; ablation of genital or venereal warts; excision of benign and malignant lesions; cosmetic and surgical repairs including vaginal prolapse; excision of diseased tissue; and haemostasis.

The electrosurgical instrument of the invention is also useful for dissection, resection, vaporisation, desiccation and coagulation of tissue and combinations of these functions with particular application in surgery on the ear, nose and throat (ENT), and more particularly procedures performed on the oropharynx, nasopharynx and sinuses. These procedures may be performed through the mouth or nose using speculae or gags or using endoscopic techniques such as functional endoscopic sinus surgery (FESS). Functional endoscopic sinus procedures may include: removal of chronically-diseased inflamed and hypertrophic mucus linings, polyps and neoplasms from the various anatomical sinuses of the skull; excision of diseased tissue; and haemostasis. Procedures on the nasopharynx may include: removal of chronically-diseased inflamed and hypertrophic mucus linings, polyps and neoplasms from the turbinates and nasal passages; submucous resection of the nasal septum; excision of diseased tissue; and haemostasis. Procedures on the oropharynx may include: removal of chronically-diseased, inflamed and hypertrophic tissue, polyps and neoplasms particularly as they occur related to the tonsil, adenoid, epi-glottic and supra-glottic regions, and salivary glands; as an alternative method to perform the procedure commonly known as laser assisted uvolopalatoplasty (LAUP); excision of diseased tissue; and haemostasis.

It is evident from the scope of applications of the invention that it has further additional applications for dissection, resection, vaporisation, desiccation and coagulation of tissue and combinations of these functions in general laparoscopic, thoracscopic and neurosurgical procedures, being particularly useful in the removal of diseased tissue and neoplastic disease whether benign or malignant.

Surgical procedures using the electrosurgical instrument of the invention may also include introducing the electrode assembly to the surgical site, whether through an artificial conduit (a cannula) or a natural conduit, which may be in an anatomical body cavity or space, or one created surgically. The cavity or space may be distended during the procedure using a fluid, or may be naturally held open by anatomical structures. The surgical site may be bathed in a continuous flow of conductive fluid such as saline solution either to fill and distend the cavity, or to create a locally-irrigated environment around the tip of the electrode assembly in a gas filled cavity. The irrigating fluid may be aspirated from the surgical site to remove products created by application of the RF energy, tissue debris or blood. The procedures may include simultaneous viewing of the site via an endoscope, or using an indirect visualisation means. An irrigated bipolar electrosurgical instrument is described in the specification of our International Patent Application No. PCT/GB96/01472.

The invention will now be described in greater detail, by way of example with reference to the drawings, in which:

FIG. 4 is a diagrammatic side elevation, partially broken away, of a second form of electrode unit constructed in accordance with the invention;

FIG. 5 is a diagrammatic side elevation of the electrode assembly of the electrode unit of FIG. 4;

Figure 1:
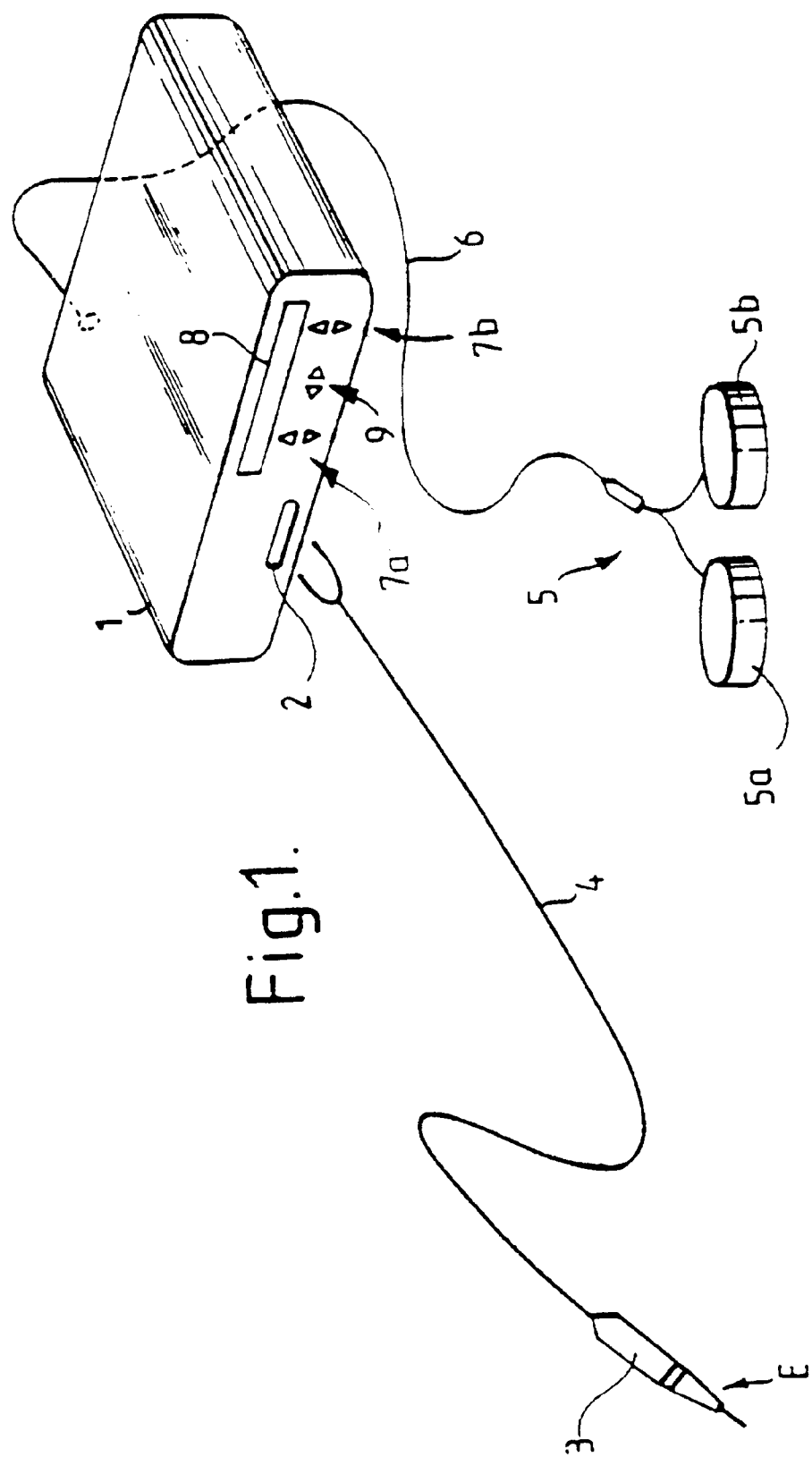
FIG. 1 is a diagram showing an electrosurgical apparatus constructed in accordance with the invention.

Referring to the drawings, FIG. 1 shows electrosurgical apparatus including a generator 1 having an output socket 2 providing a radio frequency (RF) output, via a connection cord 4, for an instrument in the form of a handpiece 3. Activation of the generator 1 may be performed from the handpiece 3 via a control connection (not shown) in the cord 4, or by means of a footswitch unit 5 connected separately to the rear of the generator 1 by a footswitch connection cord 6. In the illustrated embodiment, the footswitch unit 5 has two footswitches 5a and 5b for selecting a desiccation mode and a vaporisation mode of the generator 1 respectively. The generator front panel has push buttons 7a and 7b for respectively setting desiccation and vaporisation power levels, which are indicated in a display 8. Push buttons 9 are provided as an alternative means for selection between the desiccation and vaporisation modes.

The handpiece 3 mounts a detachable electrode unit E, such as the electrode units E1 and E4 to be described below.

Figure 2:
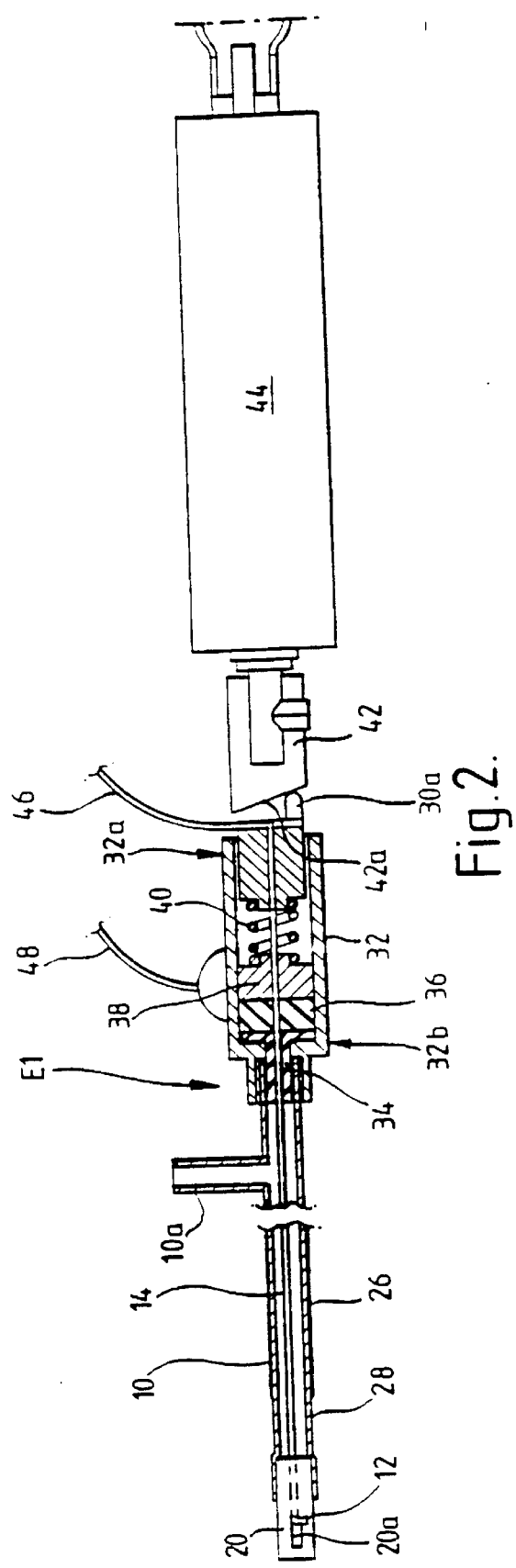
FIG. 2 is a diagrammatic side elevation, partially broken away, of a first form of electrode unit constructed in accordance with the invention.

FIG. 2 shows the first form of electrode unit E1 for detachable fastening to the electrosurgical instrument handpiece 3, the electrode unit comprising a shaft 10, which is constituted by a tube made of stainless steel. A tissue treatment (active) electrode 12 is provided at the distal end portion of the shaft 10. The active electrode 12 is provided by the distal end portion of a rod 14 made of tungsten, the active electrode extending at right angles to the rod. The rod 14 has a diameter of 0.4 to 0.6 mm. A ceramic tube 18 is fixed to the rod 14 immediately adjacent to the active electrode 12. A ceramic tip 20 is fixed within the out-turned distal end portion of the shaft 10.

As shown in FIG. 2, the active electrode 12 protrudes through a longitudinal slot 20a formed in the ceramic tip 20. That portion of the rod 14 not covered by the ceramic tube 18 is provided with an insulating sleeve 22 made of polyimide, polytetrafluoroethylene or by separate sleeves made by these two substances. A heat sleeve 24 made of polytetrafluoroethylene or polyimide, covers the adjoining regions of the ceramic tube 18 and the sleeve 22.

The major portion of the length of the shaft 10 is provided with an insulating heat shrink sleeve 26 made of polyvinylidenefluoride. The sleeve 26 does not cover the distal end portion of the shaft 10, that region of the shaft constituting a return electrode 28.

The rod 14 is mounted for reciprocal movement within the shaft 10, that end of the rod remote from the active electrode 12 being fixed to a coupling member 30 slidably mounted within one end 32a of a sleeve 32 made of stainless steel. The other end 32b of the sleeve 32 is fixed to the adjacent end portion of the shaft 10. A top hat washer 34 is located within the sleeve end 32b, the washer constituting a backing member for a silicone gland 36 and a delrin bush 38. A return spring 40 acts between the bush 38 and the coupling member 30. The rod 14 passes through apertures in the washer 34, the gland 36 and the bush 38.

An off-set shaft 30a is fixed to the end face of the coupling member 30, the free end of this shaft being engageable with an inclined end face 42a of a rotatable coupling member 42 fixed to the rotary output shaft of a motor 44. Hence, rotation of the output shaft of the motor 44 results in reciprocation of the coupling member 30 and the rod 14.

The hollow interior of the shaft 10 is connected to a transverse tubular member 10a which is connected to a suction pump (not shown), and so constitutes a suction/exhaust port. As shown in FIG. 2, the active electrode 12 is positioned at the end of an aspiration channel constituted by the annular cavity defined by the interior of the shaft 10 and the rod 14, so that vapour bubbles and/or particulate material which, in use, are formed in the region of the active electrode, can be aspirated from the region for removal via the slot 20a, the aspiration channel and the port 10a.

The RF generator 1 (not shown in FIG. 2) delivers an electrosurgical current to the electrodes 12 and 28 via connectors 46 and 48 provided respectively on the coupling member 30 and on the sleeve 32. The generator 1 includes means for varying the delivered output power to suit different electrosurgical requirements. Thus, in a first output power range of from about 140 volts to 200 volts, the active electrode 12 is used for tissue desiccation; and, in a second output power range of from about 250 volts to 600 volts, the active electrode is used for tissue removal by cutting or vaporisation. For both ranges, the voltages are peak voltages. The generator 1 may be as described in the specification of our European Patent Application 96304558.8.

This electrosurgical instrument is particularly useful for rapid tissue debulking and the removal of loose tissue. One of the problems which could be encountered when tissue is rapidly debulked using an arthoscopic electrode configuration, particularly when working in small joint spaces, is the production of vapour bubbles generated as an end product of tissue vaporisation. Such bubbles obscure vision, and can coalesce at the site of tissue application, so that an electrical circuit between the active and return electrodes having filamentary, mesh or coiled spring forms goes some way to solving this problem as it reduces the vaporisation threshold as disclosed in the specification of our International patent application No. GB97100065.

The provision of the suction pump ensures the elimination of vapour bubbles from an operation site, which is particularly advantageous during aggressive tissue debulking. The suction pump is activated only when the active electrode 12 is powered for tissue vaporisation. The pump is, therefore, pulsed so as to pull saline over the active electrode 12 (and to extract vapour bubbles and/or particulate material). This cools the active electrode 12, resulting in the collapse of the vapour pocket surrounding the active electrode. This, in turn, leads to the suction pump being turned off, thereby reducing the flow of saline over the active electrode 12. This electrode 12 then heats up again, leading to the re-formation of a vapour pocket, and the re-activation of the suction pump. This cycle then repeats until the generator 1 is turned off when the instrument is removed from the operation site.

The suction pump must be controlled so that the flow of bubbles from the active electrode 12 is balanced to the output characteristics of the RF generator 1 to prevent excessive cooling of the active electrode and a resultant increase in its vaporisation power threshold. The thermal mass of the thin, wire-form active electrode 12 is lower than that of a standard solid form active electrode, and this assists in rapidly re-established the vapour pocket around the active electrode should this collapse following excessive cooling.

The electrode unit E1 is intended primarily for use in arthroscopic surgery which requires rapid tissue debulking by vaporisation. The side-effect electrode (i.e. where the treatment axis is perpendicular to the shaft) configuration of the unit E1 is particularly advantageous for this purpose. In use, the electrosurgical instrument is manipulated to introduce the electrode assembly constituted by the active electrode 12 and the return electrode 28 into a selected operation site (e.g. within the joint space of a knee), so that the active electrode contacts the tissue to be treated, and the tissue and the electrode assembly are immersed in saline.

The footswitch 5b (or the push button 7b) is then operated to activate the generator 1. The generator 1 then provides sufficient RF power to the electrode assembly to vaporise the saline surrounding the active electrode 12, and to maintain a vapour pocket surrounding this electrode. Using a brushing technique, with firm pressure against the tissue surface, rapid debulking of the tissue is achieved. Gently touching the tissue will reduce the effect, and can be used to sculpture and smooth the residual tissue surface. With tissue engagement, the flow of irrigant away from the active electrode 12 will be reduced, the amount of reduction depending on the nature of the tissue surface, the application pressure and the suction pressure. Speed of debulking will, therefore, depend on these variables. Once the vaporisation occurs, the products will include vapour bubbles, carbon particles and tissue debris. All of these products are removed from the region of the active electrode 12, via the shaft 10 and the port 10a, by the suction pump.

All the constituents removed from the active tip are at high temperatures. This could lead to a potentially dangerous heating of the electrode shaft 10, which could cause tissue damage at the entry point. It may be, therefore, necessary to aspirate additional coolant saline from the body cavity along the inside surface of the shaft. To ensure that this saline is indeed at a safe temperature, it is taken from the rear of the return electrode 28 via a mesh filter (not shown).

In use, when the generator 1 is turned on, the motor 44 begins to rotate, causing the rod 14 to oscillate with an amplitude of 0.5 mm. The oscillation of the rod 14 within the shaft 10 provides a mechanical agitation within the shaft that is sufficient to dislodge any sublimation products which condense within the shaft. In this way, blockage of the shaft 10 is prevented, so that the instrument can be used on a continuous basis.

The oscillation of the active electrode 12 also ensures that tissue pieces removed electrosurgically by vaporisation from an operation side are morcellated electrosurgically by the oscillating electrode, thereby preventing large tissue pieces bridging the aspiration channel. Morcellation is the division of a tissue piece into many smaller pieces in order to facilitate its surgical removal.

The electrode unit E1 is also very effective in removing heated saline (distension fluid) from within a joint cavity. The risk of hot distension fluid occurs primarily during power application to reach the vaporisation threshold. Once the threshold has been reached, the power requirement falls by 30–50%.

Whilst aspiration from the region of the active electrode 12 will remove heated saline from the body cavity, and remove any risk of overheating through prolonged activation under conditions where the vaporisation threshold is not reached, the cooling effect and disruption of vapour pockets created around the active electrode will increase the vaporisation threshold. A vicious cycle can, therefore, be created, wherein the more suction applied at the active electrode 12, the more power required to reach the vaporisation threshold, and the greater the risk of heating. The other factor influencing the vaporisation threshold is the ratio of return: active contact area, and the insulation separation between the active electrode 12 and the return electrode 28. The size of the active electrode 12 and the insulation separation, must, therefore, be reduced to the minimum necessary to achieve the function in order to offset the effects of aspiration in elevating the power threshold of vaporisation.

The specification of our International Patent Application GB97100065 discloses techniques for controlling the vaporisation threshold by employing active electrode designs which assist in capturing vapour pockets and preventing cooling of the active electrode application site by screening from the flow of irrigant provided by channels in an endoscope. An alternative method of reducing the vaporisation power threshold is to pulse the suction pressure, thereby allowing the threshold to be attained between pulses. Such pulses may be synchronised with the output features of the RF generator 1 to provide power bursts during active suction to sustain the vapour pocket, and clear any tissue occluding the apertures in the active electrode 12.

A known technique in arthroscopic surgery is to apply suction through a mechanical, tissue-nibbling device so that soft tissue present in the joint space, such as the infrapatellar fat pad, can be held in position within the nibbler jaws by suction whilst it is progressively "nibbled away".

Attracting tissue to the active electrode 12 of the electrode unit E1 has a similar effect as, for the reasons already given above, compliant tissue adhering to the active electrode will result in a reduction of the vaporisation power threshold. Adherent tissue will be rapidly vaporised, and small tissue particles produced during vaporisation will be aspirated from the application site.

Because of its speed of debulking and side-effect configuration, the electrode unit E1 also has advantages in urological surgery as an EVAP technique for use in conjunction with a resectoscope. A resectoscope electrode unit is introduced very differently, in that is mounted on an endoscope prior to passage of the assembled instrument through a working sheath via the urethra. The proximal end of the electrode unit is connected to a trigger assembly and an electrical contact which is integral with the resectoscope. By this means, the electrode unit E1 can be moved back and forth through a defined range of motion by operating the trigger mechanism. As the electrode unit E1 is assembled prior to introduction, the size of the tip is not constrained by working channel dimensions, but rather by the diameter of the working sheath which can be up to 10 mm. Part of this diameter is occupied by the support wires to the electrode unit E1, which wires are commonly bent in a downward angle, with respect to the endoscopic image, to the working tip, so that they do not interfere with either visulation or its operation. Because of the reciprocatory movement of the rod 14, the active electrode 12 operates over a length lying within the range of from 3 mm to 4 mm and a width lying in the range of from 2 mm to 3 mm, and this size is necessary for urological surgery given that, on average, 20–30 grammes of prostate tissue must be removed.

Because of the reservoir effect of the urinary bladder, and the mounting of the endoscope to view the tip of the active electrode 12 from below, bubble generation during vaporisation is less of a problem during endoscopic urology, as the bubbles flow away from the endoscope to accumulate in the bladder. Nevertheless, the use of the electrode unit E1 substantially reduces the possibility of bubble generation causing problems.

Although the electrode unit E1 is intended primarily for use in the vaporisation of tissue it can also be used for desiccation, particularly of synovial membranes or to separate muscle attachments. In this case, once the electrode assembly of the electrode unit E1 has been introduced into a selected operation site, the RF generator 1 is actuated using the footswitch 5a or the push button 7a. The generator 1 will then provide sufficient RF power to the electrode assembly to maintain the saline adjacent to the active electrode 12 substantially at its boiling point without creating a vapour pocket surrounding that electrode. The instrument can then be manipulated by moving the active electrode 12 across the surface of the tissue to be treated in a side-to-side "painting" technique.

The electrode unit E1 can also be used for delivering a blended power output. This is achieved by automatically alternating the output of the RF generator 1 between the desiccation and vaporisation power levels, more haemostasis being produced then is possible in the vaporisation mode. As a consequence, the speed of tissue debulking is reduced, but the increased haemostasis is useful when cutting or debulking vascular tissue structures. Alternatively, the output of the RF generator 1 can be pulsed at the vaporisation power level, without cycled activation of the desiccation mode. This produces a less aggressive tissue vaporisation than occurs in the vaporisation mode, with a consequent reduction in both bubble formation and the risk of tissue charring.

The active electrode 12 of the unit E1 is a side effect electrode (i.e. its treatment axis is perpendicular to the shaft). Axial agitation is advantageous with such electrodes, in that the entire electrode can be brought into contact with tissue. As a result, the exposed area can be made very small, allowing operation at lower powers and less at higher saline flow rates.

Figure 3:
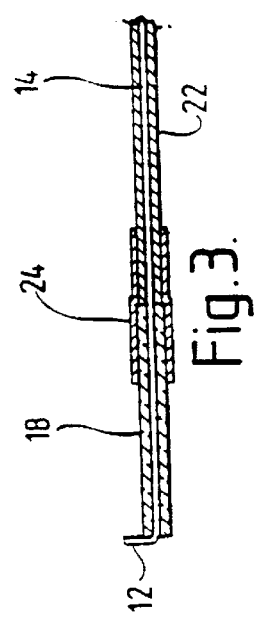
FIG. 3 is a diagrammatic side elevation of the electrode assembly of the electrode unit of FIG. 2.

FIGS. 4 and 5 show the second form of electrode unit E2. This instrument is a modification of that shown in FIGS. 2 and 3, and so like reference numerals will be used for like parts, and only the modifications will be described in detail. There are two main modifications, the first being to the drive to the rod 14, and the second to the configuration of the active electrode 12.

In the first modification, the motor 44 rotatably drives the rod 14 via a coupling. assembly 42. As with the embodiment of FIGS. 2 and 3, the rod 14 passes through aligned apertures in the washer 34, the gland 36 and the delrin bush 38. The bush 38 is somewhat longer than the equivalent bush of the embodiment of FIGS. 2 and 3 extending to the end 32a of the sleeve 32. A slip ring 46a is provided to connect the connector 46 to the rod 14.

The other main modification is that the active electrode 12 (the free end of the tungsten rod 14—in this embodiment of 0.5 mm diameter) is bent back over the free end of the ceramic tube 18. The turned-back portion 12a of the electrode 12 constitutes a side effect electrode. An apertured region 20a is formed between the ceramic tip 20 and the active electrode 12, this region loading to the aspiration channel defined by the interior of the shaft 10.

Another modification is that the rod 14 is a flexible drive rod whose distal end portion is off-set with respect to the central longitudinal axis of the shaft 10. In use, when the generator 1 is turned on, the motor 44 begins to rotate, causing the rod 14 to rotate within the shaft 10 This rotation provides a mechanical agitation that is sufficient to dislodge any sublimation products which condense within the shaft. The off-set of the rod 14 results in an unstable oscillation being set up in the rod, which sweeps adherent tissue debris from the inner wall of the shaft 10.

Figure 6:
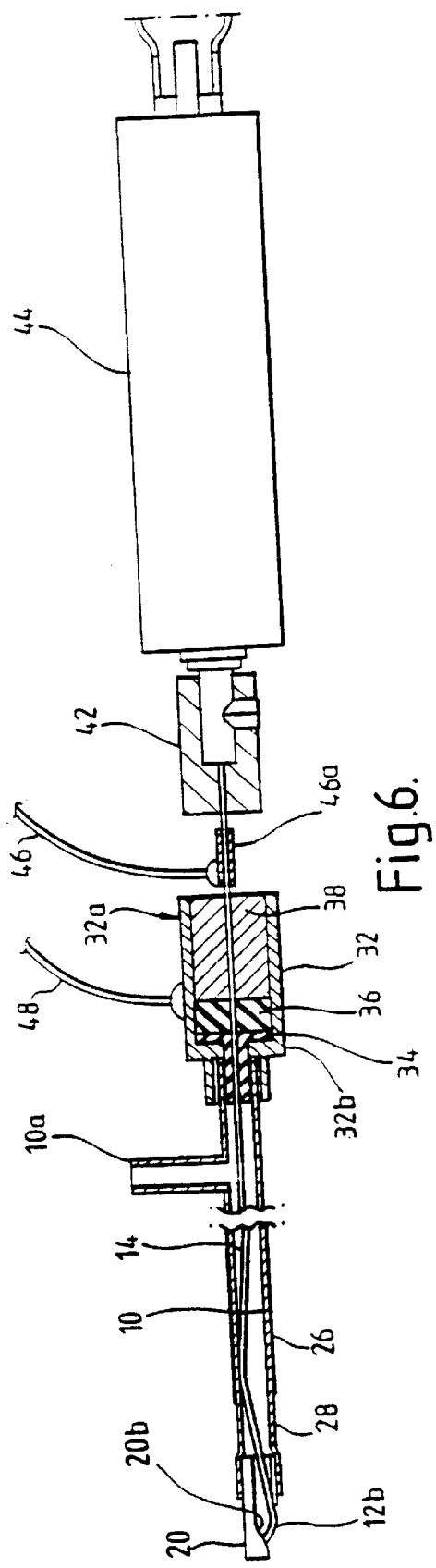
FIG. 6 is a diagrammatic side elevation, partially broken away, of a third form of electrode unit constructed in accordance with the invention.
Figure 7:
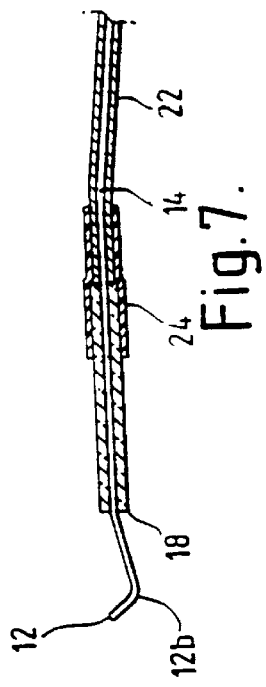
FIG. 7 is a diagrammatic side elevation of the electrode assembly of the electrode unit of FIG. 6.

FIGS. 6 and 7 show the third form of electrode unit E3. This unit E3 is a modification of the unit E2, so like reference numerals will be used for like parts, and only the modifications will be described in detail. The main modification is to the configuration of the active electrode assembly. Thus, as shown in FIG. 7, the active electrode 12 is shaped like a crank handle, and defines an elbow 12b which is off-set from the axis of the ceramic tube 18. The ceramic tip 20 is formed with an inclined cam surface 20b which, in use, engages with the elbow 12b to force the tip of the active electrode 12 outwardly, and to ensure better tissue engagement. This crank handle configuration of the active electrode 12 also ensures that, as the tip rotates, the elbow 12b is pushed around the inner surface of the ceramic tip 20, thereby removing debris which would otherwise tend to build up there.

Figure 8:
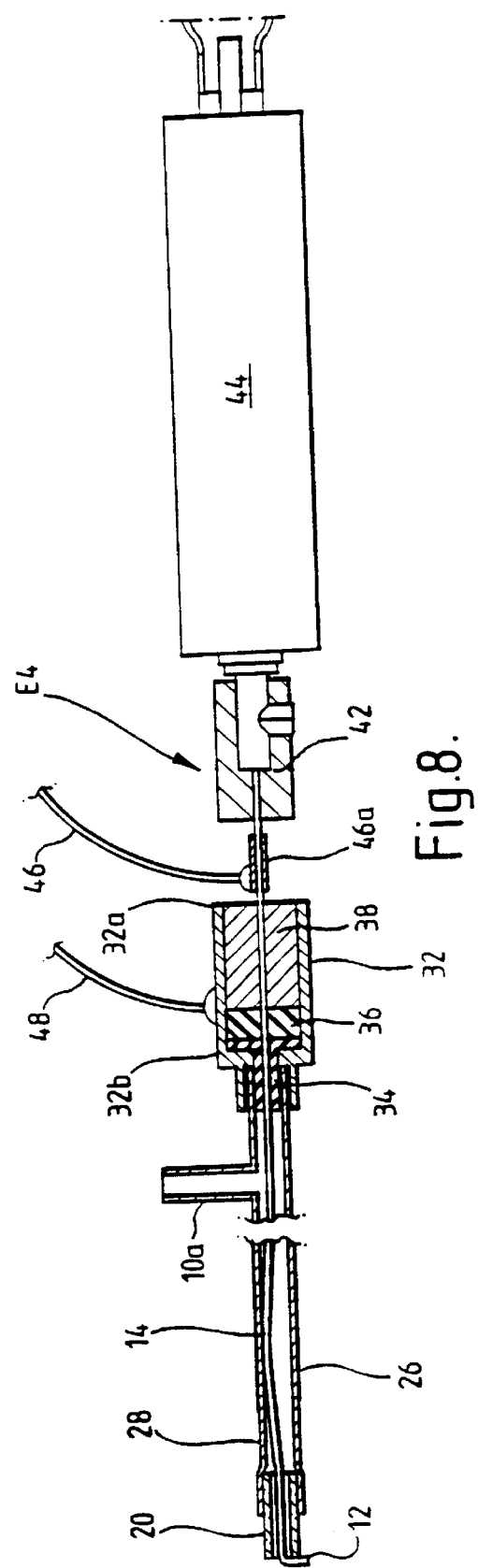
FIG. 8 is a diagrammatic side elevation, partially broken away, of a fourth form of electrode unit constructed in accordance with the invention.
Figure 9:
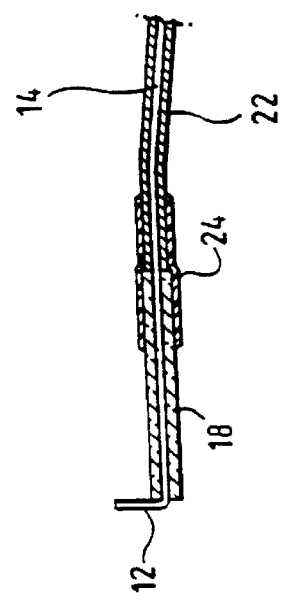
FIG. 9 is a diagrammatic side elevation of the electrode assembly of the electrode unit of FIG. 8.

FIGS. 8 and 9 show the fourth form of electrode unit F4. This unit E4 is also a modification of the unit E2, so like reference numerals will be used for like parts, and only the modifications will be described in detail. Here, the main modification is to the configuration of the active electrode 12 which, in this case, is an end effect electrode, being constituted by a simple hook-shaped end portion 12a at the end of the rod 14.

As with the embodiments of FIGS. 4 and 5, the rod 14 is a flexible drive rod whose distal end portion off-set with respect to the central longitudinal axis of the shaft 10.

As has already been described, the adherence of tissue over the active electrode 12 may induce a steady state condition, and the aspiration method must allow for removal of unvaporised tissue particles whilst not quenching vapour pocket formation. Rotation of the active electrode 12 of the electrode units E2 to E4 provides several advantages to overcome these performance issues. Thus, rotating the active electrode 12 increases the effective size of the electrode, as far as tissue contact area is concerned, for one complete rotation, whilst reducing the physical size of the active electrode. Reducing the size of the active electrode 12 reduces the vaporisation power threshold to a degree sufficient to enable aspiration along the axis of rotation when the generator control method is employed.

The introduction of rotation and aspiration through the active electrode 12, or more accurately through a channel within the range of motion of the active electrode, prevents the steady state being reached, and so prevents tissue bridging. This is achieved as tissue temporarily obstructing the aspiration channel is always treated, as opposed to positioning aspiration channels outside the range of motion of the active electrode 12, in which case only tissue adjacent to that obstructing the aspiration channel would be treated.

Given that the aspiration channel is required to cope with unvaporised tissue, the active electrode 12 is only required to incise the tissue such that the tip of the tissue in the aspiration channel is detached from the body of the tissue and then aspirated through the channel. Ideally, the truncated portion of tissue is also morcellated or partially vaporised by the active electrode 12 to reduce the size of tissue pieces. This morcellation is accomplished by introducing an off-set in the drive shaft/connector to the active electrode 12 which rotates in the aspiration channel of larger internal diameter than the external diameter of the connector, a feature which has additional advantages in preventing blocking of the aspiration channel, as is described below.

The relative contributions of tissue incision or morcellation and tissue vaporisation to the overall tissue debulking process can be controlled by the interaction of the bore of the terminal aspiration channel, the suction pressure and the bulk of the active electrode 12. Owing to the overall size constraints on the external diameter of the instrument it is, in general, the diameter of the drive rod 14 whose distal tip forms the active electrode 12 and which, therefore, also provides the means of electrical connection to the active electrode, which determines whether tissue removal occurs primarily by incision/morcellation or vaporisation. Typically a drive rod 14 (and hence active electrode 12) formed from 0.2–1.0 mm diameter tungsten wire provides incision/morcellation, and a drive rod active electrode formed from 0.5 mm diameter tungsten wire primarily provides vaporisation. The incision/morcellation technique has advantages when dealing with soft friable tissue, whereas the vaporisation technique has advantages when application is made to dense fibrous or cartilaginous tissue. The design can, therefore, be optimised for the type of tissue encountered during use in particular surgical specialities or, alternatively, a multi functional design with a drive rod and active electrode typically formed from 0.4–0.6 mm tungsten can be used.

For all four electrode units E1 to E4, agitation within the aspiration shaft 10 significantly reduces the risk of blockage, either by morcellated tissue, sublimated products of vaporisation or both. This can be accomplished by axial or rotary motion of the rod 14 which is positioned within the aspiration channel, with or without other means of fluid agitation, including the cycling of suction pressure, which may be provided as an integral feature of generator output, control of suction, and sonic pressure waves. To enhance the effect of agitation, it is beneficial to construct the drive rod 14 from a lubricious material to reduce adherence.

Each of the electrode units E1 and E4, has the additional advantage that the aspiration in the region of the active electrode 12 restricts the flow of convection currents in the saline surrounding the electrode assembly. As the power threshold required to reach vaporisation is dependent on the power dissipation of the active electrode 12 and the flow characteristics around it, the power threshold is dependent upon the maximum rate of convection. Consequently, the restriction of the convection currents reduces the power threshold and/or permits the use of higher saline flow rates, and this is advantageous as it enables the use of a cheaper RF generator, as well as avoiding problems such as dissipation within the instrument, and catastrophic overheating of the active electrode. It also facilitates control of the generator once vaporisation commences. The importance of power threshold of vaporisation is discussed in greater detail in the specification of our International Patent Application No. GB97/00065.

Moreover, each of the electrode units E1 to E4 is such as to prevent tissue bridging, as the tendency for tissue to obstruct the aspiration channel is, in each case, obviated by the movement of the active electrode ensuring that such tissue is treated. The movement of the active electrode 12 also ensures tissue morcellation, though this is effected by electrosurgery rather than by mechanical cutting.

It is a feature of each of the electrode units E1 to E4 that pieces of morcellated tissue separated from a surgical site will be drawn into the aspiration channel by the suction pressure. Should such pieces be too large to enter the aspiration channel, they will be reduced in size by a combination of the mechanical action of the agitated electrode 12 and the electrosurgical action created by the positioning of the return electrode 28 in relation to the aspiration channel. In the limit, the spacing of the return electrode 28 relative to the motion of the agitated electrode 12 can be adjusted to allow a controlled level of periodic arcing between the two. This aspect permits control of the relative strength of the mechanical and electrosurgical actions in keep the aspiration channel clear. This aspect is described in greater detail in the specification of our British Patent Application It will be apparent that modifications could be made to the electrode units described above. For example, instead of providing an off-set drive rod 14, this rod could be loosely coiled so that the coils lie against the inner wall of the aspiration channel, whereby, during rotation, a worm screw action occurs to encourage proximal movement of tissue debris, as well as cleaning of the inner wall of the channel.

The motor 44 of each of the embodiments would be powered by the RF generator 1. This has the advantage that the motor 44 can be controlled by means that require the RF output voltage to exceed the vaporisation power threshold before sufficient power is delivered to energise the motor. Control means for the purpose could be mounted with the motor 44 within the handpiece 3.

It would also be possible to introduce axial motion during rotation. Thus, for the electrode unit E4, the simple 90° hook form active electrode 12 can rotate on a bearing surface provided by the distal end face of the ceramic tube 18, this end face being provided with ratchet teeth features. Thus, as the rod 14 rotates, the hook-shaped end portion 12a moves in and out as it engages and disengages the ratchet teeth, this axial movement being permitted by the off-set flexible drive rod 14 repeatedly elongating and shortening.

As an alternative to an electric motor, each of the units E1 to E4 could be powered by a fluid drive generated through a rotary vane or similar apparatus, which, in turn, may be powered by the suction means.

It is also possible to power the rotary drive by the RF generator 1, so that an integral and interactive system of the rotary drive, the active electrode 12, the RF generator and the suction means is provided.

The upper limit of the speed of rotation of the units E2 to E4 is defined at that level which elevates the vaporisation power threshold beyond the output range of the RF generator 1, which will, in turn, be dependent upon the geometry of the active electrode 12. Typically, the speed of tissue removal is increased with increased rotary speed when primarily employing the incision/morcellation technique, and is increased with decreased rotary speed when primarily employing the vaporisation technique. It is, therefore, evident that, in a multi-functional design, it is advantageous for the user to vary the rotary speed depending on the nature of the tissue being treated. To this end, a typical range of rotary speeds would be from 100 revs/min to 1000 revs/min.

With the rotary action electrode units E2 to E4, the effective size of the active electrode 12 is increased, and a significant aspect is the incision of tissue. The active electrode 12 is fabricated from the distal end of the drive rod 14, so simple wire form electrodes meet these performance requirements. The only drawback of these simple electrode forms is that asymmetry of the tissue contact can make it difficult to maintain an accurate location on a tissue surface, particularly when that surface is comprised of more fibrous or more dense tissue.

If the wire form active electrode 12 protrudes from the ceramic tube 18, for example in a simple loop form as with the electrode unit E2, then the potential exists for the loop to excise tissue pieces too large for aspiration through the distal opening of the aspiration channel. Should this occur, the exposed distal end of the drive rod 14 within the aspiration channel performs an important function in morcellating and vaporising such tissue pieces, so that they are reduced in size sufficiently to enter the aspiration channel. This function is enhanced by the eccentric motion of the drive rod 14 within the aspiration channel.

Whilst the amount of protrusion of the active electrode 12 from the distal end of the ceramic tube 18 is governed by the rules described in our International Patent Application GB96/01473, the effect of aspiration in increasing vaporisation threshold changes these rules. The other performance factor governing the dimension of the active electrode 12 is similar to that defining the diameter of the wire. Thus, the thinner wire forms, which are used on soft tissue, can protrude from the distal end of the ceramic tube 18 in the treatment axis; whilst the thicker wire forms, which are used on more dense tissue, ideally extend beyond the distal end of the ceramic tube in the treatment axis by an amount not exceeding the diameter of the wire.

The active electrode 12 may also take on more convoluted or more complex generally planar forms of end effect electrodes and generally axial forms for side effect electrodes, for example coils, spirals, meshes or multiple spokes.

Our International Patent Application GB96/01472 describes a technique of introducing a conductive fluid to the region of a tissue treatment (active) electrode in order to define, in use, a conductive fluid path between the active electrode and a return electrode. The electrode units E1 to E4 of the present invention could be modified to incorporate those features. In particular, these units could be modified for use in gaseous operating environments, either on the surface of a body or within body cavities.

The specification of our British Patent Application 9612993.7 describes a technique of aspiration in the vicinity of a tissue treatment (active) electrode, wherein the suction pressure is controlled by generator output features in order to facilitate vaporisation by intermittently lowering the vaporisation threshold by cessation of suction flow. The techniques could advantageously be incorporated in the electrode units E1 to E4, both to ensure the vaporisation threshold is exceeded between suction pulses, and as a result of the suction pulsing assisting in preventing blockage of the aspiration channel.

As a suction pulse is initiated only once the vaporisation threshold has been exceeded, tissue can only be attracted to the active electrode once the threshold is exceeded by activation remote from the tissue within the surrounding distension medium. It is known that the vaporisation threshold is lowered once tissue is engaged by the active electrode. It is, therefore, advantageous for suction to be applied initially without RF activation as a variable time delay feature.

In summary the electrosurgical instrument of the invention has the following advantageous features:30

1. A small active electrode surface which is able to treat large tissue areas by virtue of active electrode movement.
2. A small active electrode to enable vaporisation, despite the cooling effects created by aspiration.
3. A mechanical movement at the active electrode tip, compatible with material removal within the aspiration channel.
4. Aspiration operation is dependent upon the vaporisation condition.
5. At least the outside of the shaft 10 is coated with a non-stick material such as polytetrafluoroethylene—ideally the inside of the shaft as well.
6. Active electrode tip movement occurs across the face of the aspiration channel, so that any lodged tissue is electrosurgically morcellated.
7. Active electrode agitation is dependent upon the vaporisation condition.
8. Discontinuities within the agitator rod ensure that the internal surfaces of the shaft are cleaned; or the rod flexes sufficiently to create the same effect.
9. A ceramic-to-ceramic interface at the active electrode tip ensures that the internal circumference of the outer ceramic is wiped by the inner ceramic.
10. The agitator rod is independently insulated in ceramic at its tip.
11. Offset rotary action for a side-effect electrode to enable flat surface engagement.

What is claimed is:

1. An electrosurgical instrument for the treatment of tissue in the presence of an electrically-conductive fluid medium, the instrument comprising:
    an instrument shaft,
    a tissue treatment electrode mounted at the distal end of the shaft,
    removal means comprising a channel formed within the instrument shaft, and
    an apertured portion through which matter can be aspirated by the removal means from the region surrounding the tissue treatment electrode, the removal means extending from the apertured portion,
    wherein the channel is provided with agitation means movable relative thereto, the agitation means being a rod mounted within and movable relative to the instrument shaft, the rod being rotatable within the channel and formed with a portion off-set from the longitudinal axis of the instrument shaft,
    whereby the off-set portion rotates within the channel around the longitudinal axis of the instrument shaft when the rod is rotated within the channel.

2. An electrosurgical instrument as claimed in claim 1, further comprising drive means for moving the tissue treatment electrode relative to the distal end of the shaft.

3. An electrosurgical instrument as claimed in claim 1, further comprising a return electrode which is electrically insulated from the tissue treatment electrode by insulation means, the tissue treatment electrode being exposed at the distal end of the instrument, and the return electrode having a fluid contact surface spaced proximally from the exposed end of the tissue treatment electrode.

4. An electrosurgical instrument as claimed in claim 3, wherein the tissue treatment electrode is movable cyclically relative to the return electrode so as to move the tissue treatment electrode into, and out of, at least one position in which arcing occurs between the tissue treatment and return electrode.

5. An electrosurgical instrument as claimed in claim 3, wherein the agitation means is constituted by a rod mounted within, and movable relative to, the instrument shaft.

6. An electrosurgical instrument as claimed in claim 5, wherein the tissue treatment electrode is constituted by the distal end portion of the rod.

7. An electrosurgical instrument as claimed in claim 6, wherein the rod is constituted by a tungsten wire having a diameter in the range of from 0.2 mm to 1.0 mm.

8. An electrosurgical instrument as claimed in claim 7, wherein the tungsten wire has a diameter in the range of from 0.4 mm to 0.6 mm.

9. An electrosurgical instrument as claimed in claim 6, wherein the tissue treatment electrode is angled with respect to the longitudinal axis of the instrument shaft.

10. An electrosurgical instrument as claimed in claim 9, further comprising an insulating sleeve surrounding the rod proximally of said angled end portion.

11. An electrosurgical instrument as claimed in claim 10, wherein the insulating sleeve is a ceramic sleeve.

12. An electrosurgical instrument as claimed in claim 9, wherein the angled end portion of the rod is at right-angles to the longitudinal axis of the instrument shaft, and the tip of the angled end portion constitutes the tissue contacting portion of the tissue treatment electrode.

13. An electrosurgical instrument as claimed in claim 6, wherein the insulation means comprises an insulation member provided at the distal end of the instrument shaft, the insulation member defining said apertured portion.

14. An electrosurgical instrument as claimed in claim 13, wherein the insulation member is formed with a slot which constitutes the apertured region, the tissue treatment electrode passing through the slot.

15. An electrosurgical instrument as claimed in claim 13, wherein the apertured portion is constituted by a gap between the tissue treatment electrode and the insulation member.

16. An electrosurgical instrument as claimed in claim 6 further comprising drive means for moving the tissue treatment electrode relative to the distal end of the shaft, and wherein the drive means is such as to reciprocate the rod within the channel.

17. An electrosurgical instrument as claimed in claim 16, wherein the drive means is constituted by a motor and coupling means for converting the rotary output of the motor into reciprocatory movement of the rod.

18. An electrosurgical instrument as claimed in claim 6 further comprising drive means for moving the tissue treatment electrode relative to the distal end of the shaft, and wherein the drive means is such as to rotate the rod within the channel.

19. An electrosurgical instrument as claimed in claim 18, wherein an electric motor constitutes the drive means.

20. An electrosurgical instrument as claimed in claim 18, wherein the rod is formed with a portion off-set from the longitudinal axis of the instrument shaft.

21. An electrosurgical instrument as claimed in claim 18, wherein the angled end portion of the rod is at right-angles to the longitudinal axis of the instrument shaft, and the distal end surface of said angled end portion constitutes the tissue contacting portion of the tissue treatment electrode.

22. An electrosurgical instrument as claimed in claim 18, wherein the angled end portion of the rod makes an acute angle with the longitudinal axis of the instrument shaft.

23. An electrosurgical instrument as claimed in claim 18, wherein the angled end portion of the rod is bent back around the distal end portion of the insulating sleeve.

24. An electrosurgical instrument as claimed in claim 8, further comprising an RF generator having a bipolar output connected to the tissue treatment electrode and the return electrode.

25. An electrosurgical instrument as claimed in claim 24, wherein the pump is controlled in dependence upon the output characteristics of the RF generator.

26. An electrosurgical instrument as claimed in claim 1, wherein the channel is defined by the instrument shaft.

27. An electrosurgical instrument as claimed in claim 1, wherein the removal means further comprises a pump connected to the channel at a region thereof remote from the apertured portion of the instrument.

28. An electrosurgical instrument as claimed in claim 27, wherein the pump is activated cyclically whereby matter is aspirated by the removal means in a pulsed fashion.

29. An electrosurgical instrument as claimed in claim 28, wherein the pump is activated only when the tissue treatment electrode is powered for tissue vaporisation.

30. An electrosurgical instrument for the treatment of tissue in the presence of an electrically-conductive fluid medium, the instrument comprising:

an instrument shaft, a tissue treatment electrode mounted at the distal end of the shaft, a return electrode electrically insulated from the tissue treatment electrode by an insulation member, removal means, and drive means for moving the tissue treatment electrode relative to the distal end of the shaft, the instrument having an apertured portion through which matter can be aspirated by the removal means from the region surrounding the tissue treatment electrode, the removal means comprising a channel formed within the instrument shaft and leading from the apertured portion, the channel being provided with agitation means movable relative thereto, the agitation means being constituted by a rod mounted within, and movable relative to, the instrument shaft, the rod including an end portion angled with respect to the instrument's shaft's longitudinal axis, the tissue treatment electrode being constituted by the distal end portion of the rod, the drive means rotating the rod within the channel, wherein the angled portion of the rod makes an acute angle with the longitudinal axis of the instrument shaft, and wherein the insulation member is provided with an inclined cam surface which is engagable with the apex of the angled end portion of the rod.

31. An electrosurgical instrument for the treatment of tissue in the presence of an electrically-conductive fluid medium, the instrument comprising:

an instrument shaft, a tissue treatment electrode mounted at the distal end of the shaft and being exposed at the distal end of the instrument, removal means, an apertured portion through which matter can be aspirated by the removal means from the region surrounding the tissue treatment electrode, the removal means comprising a channel formed within the instrument shaft and leading from the apertured portion, the channel being provided with agitation means therein and movable relative thereto, the agitation means being a rod having a portion off-set from the longitudinal axis of the shaft, the rod and off-set portion being rotatable within the channel, drive means for moving the agitation means, whereby the tissue treatment electrode is moved relative to the distal end of the shaft, and a return electrode which is electrically insulated from the tissue treatment electrode by insulation means and having a fluid contact surface spaced proximally from the exposed end of the tissue treatment electrode, an RF generator having a bipolar output connected to the tissue treatment electrode and the return electrode, wherein the RF generator supplies energy to the drive means.

* * * * *